United States Patent
Carlson et al.

(10) Patent No.: US 6,529,772 B2
(45) Date of Patent: *Mar. 4, 2003

(54) HEART RATE VARIABILITY AS AN INDICATOR OF EXERCISE CAPACITY

(75) Inventors: Gerrard M. Carlson, Champlin, MN (US); Veerichetty A. Kadhiresan, Lino Lakes, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 09/888,726

(22) Filed: Jun. 25, 2001

(65) Prior Publication Data

US 2001/0037069 A1 Nov. 1, 2001

Related U.S. Application Data

(60) Division of application No. 09/419,659, filed on Oct. 18, 1999, now Pat. No. 6,301,499, which is a continuation-in-part of application No. 09/093,118, filed on Jun. 8, 1998, now Pat. No. 6,026,320.

(51) Int. Cl.[7] .................................................. A61B 5/04
(52) U.S. Cl. .......................... 600/510; 600/521; 607/25
(58) Field of Search ................................ 600/510, 516, 600/519–521; 607/25

(56) References Cited

U.S. PATENT DOCUMENTS

| 5,466,245 | A |   | 11/1995 | Spinelli et al. |   |
|---|---|---|---|---|---|
| 5,603,331 | A |   | 2/1997 | Heemels et al. |   |
| 6,026,320 | A | * | 2/2000 | Carlson et al. | ............. 600/510 |
| 6,301,499 | B1 | * | 10/2001 | Carlson et al. | ............. 600/510 |

OTHER PUBLICATIONS

Singer, et al., "Low Heart Rate Variability and Sudden Cardiac Death", *Journal of Electrocardiology*, Supplemental Issue 1988, S45–S55.

Ori, et al., "Heart Rate Variability Frequency Domain Analysis", *Cardiology Clinics*, vol. 10, No. 3, Aug. 1992, pp. 499–537.

* cited by examiner

*Primary Examiner*—Jeffrey R. Jastrzab
(74) *Attorney, Agent, or Firm*—Thomas J. Nikolai; Nikolai & Mersereau, P.A.

(57) ABSTRACT

Based upon patient studies indices a high degree of correlation was found between HRV and $VO2_{max}$, i.e., the patient's exercise capacity. Based on this finding, a pacing therapy optimization protocol for treating patients with CHF has been devised. The protocol involves first pacing the patient's heart with a pacemaker programmed to operate in a first mode for a predetermined time period and then collecting electrogram data from which a HRV index is derived. The mode is then changed and the steps repeated until all possible modes have been utilized. At that time, a determination is made as to which of the modes is associated with the largest HRV index and the pacemaker is then programmed to function in that mode. Alternatively, the method of the present invention can be applied to changes in drug therapy instead of or in combination with pacing therapy. By the plotting the HRV index computed in the manner described, the efficacy of a change in therapy on patient exercise capacity can be assessed.

1 Claim, 7 Drawing Sheets

FIG. 5 AFTER PACING

FIG. 4 BEFORE IMPLANT

THE HEART RATE VARIABILITY FOOTPRINT

FIG. 6

FIG. 7

HEART RATE VARIABILITY AS AN INDICATOR OF EXERCISE CAPACITY

CROSS REFERENCE TO RELATED APPLICATIONS

This application is a divisional of application Ser. No. 09/419,659 now U.S. Pat. No. 6,301,499, which application is a continuation-in-part of application Ser. No. 09/093,118, filed Jun. 8, 1998 now U.S. Pat. No. 6,026,320.

BACKGROUND OF THE INVENTION

I. Field of the Invention

This invention relates generally to a method and apparatus for assessing patient well-being, and more particularly to a method and apparatus for indirectly determining a patient's peak oxygen uptake ($VO2_{max}$) by measuring his/her heart rate variability (HRV).

II. Discussion of the Prior Art

It is known in the art that HRV, i.e., the beat-to-beat variance in sinus cycle length over a period of time, is a predictor of mortability and morbidity. Patients exhibiting low HRV show a significantly increased risk of sudden cardiac death. See "Heart Rate Variability" by Zsolt Ori, et al., *Cardiology Clinics*, Vol. 10, No. 3, August 1992, pp. 499–537 and "Depressed Heart Rate Variability As An Independent Predictor of Death in Chronic Congestive Heart Failure Secondary to Ischemic or Idiopathic Dilated Cardiomyopathy" by Piotr Ponikowski, et al., *The American Journal of Cardiology*, Vol. 79, Jun. 15, 1997, pp. 1645–1650. See also "Correlations Among Time and Frequency Domain Measures of Heart Period Variability Two Weeks After Acute Myocardial Infarction" by J. Thomas Bigger et al., *The American Journal of Cardiology*, Vol. 69, Apr. 1, 1992. In addition, the Spinelli et al. U.S. Pat. No. 5,466,245 provides a very detailed method for automatically determining AV delay based on evaluating a frequency domain measure of heart rate variability (HRV).

In the Heemels et al. U.S. Pat. No. 5,603,331, assigned to applicant's assignee, a method and apparatus is described for efficiently processing, logging and disseminating essential features relating to HRV accumulated from a continuous, long-term monitoring of cardiac activity. As pointed out in that patent, the method sufficiently conserves data memory, program memory and power consumption that it may be incorporated within an implantable pacemaker or defibrillator to log a 24-hour period of cardiac activity accumulated for subsequent telemetry to an external monitor. The patent further describes a method of processing and displaying HRV data in a manner that is readily understandable by clinicians which provides an improved graphical contrast between normal and abnormal HRV patterns.

Further studies which we have recently conducted on several patients has revealed a high correlation between HRV and a patient's exercise capacity as measured by $VO2_{max}$. Based upon this realization, a method has been established for indirectly assessing a patient's maximum oxygen uptake by computing the standard deviation of five minute mean RR intervals, i.e., the SDANN Index. In an alternative approach, a two-dimensional histogram array is plotted with RR intervals along one axis and the absolute value of the time difference between successive RR intervals plotted along the second axis. By measuring the area on the plot occupied by the two-dimensional histogram, $VO2_{max}$ can be estimated.

SUMMARY OF THE INVENTION

In accordance with a first aspect of the invention, an estimation of a patient's maximum oxygen uptake can be derived by the following method:

First, a patient's ECG waveform is sensed and recorded over a 24-hour period. In a pacemaker implementation, the whole 24-hour recording is not possible. Instead, the R-R interval is calculated in real time (on the fly). The recording is then analyzed and a determination is made as to the average length of normal RR intervals in 288 five-minute intervals. When the standard deviation of the 288 averages is computed, it yields an index exhibiting a high correlation with the patient's peak oxygen consumption.

In an alternative method, rather than computing the SDANN Index, the length of RR intervals in the recorded ECG waveform during a plurality of time segments of a predetermined length are measured and the absolute value of the time difference between successive RR intervals is determined. By plotting this data as a two-dimensional histogram and then measuring the area on the plot occupied by the two-dimensional histogram, the patient's peak oxygen uptake can be inferred. That is to say, studies have shown that there is a high correlation between the area or "footprint" of the histogram and the patient's peak oxygen uptake.

Irrespective of which of the above methods is employed, the information arrived at can be utilized in assessing the efficacy of a given mode of drug therapy or electrical cardiac stimulation on a patient's exercise capacity. By plotting the HRV Index computed over predetermined time intervals in accordance with the first method or the footprint area determined in accordance with the alternative method, trends in a patient's peak oxygen uptake resulting from a predetermined therapy regimen can be determined and used in adjusting the regimen. This is achieved without the need for conducting a breath-by-breath analysis of ventilatory flow and subjecting the patient to a treadmill test or the like.

DESCRIPTION OF THE DRAWINGS

FIG. 8 (c) is a plot average week SDANN index over the same 52-week period.

DESCRIPTION OF THE PREFERRED EMBODIMENT

Figure 1:
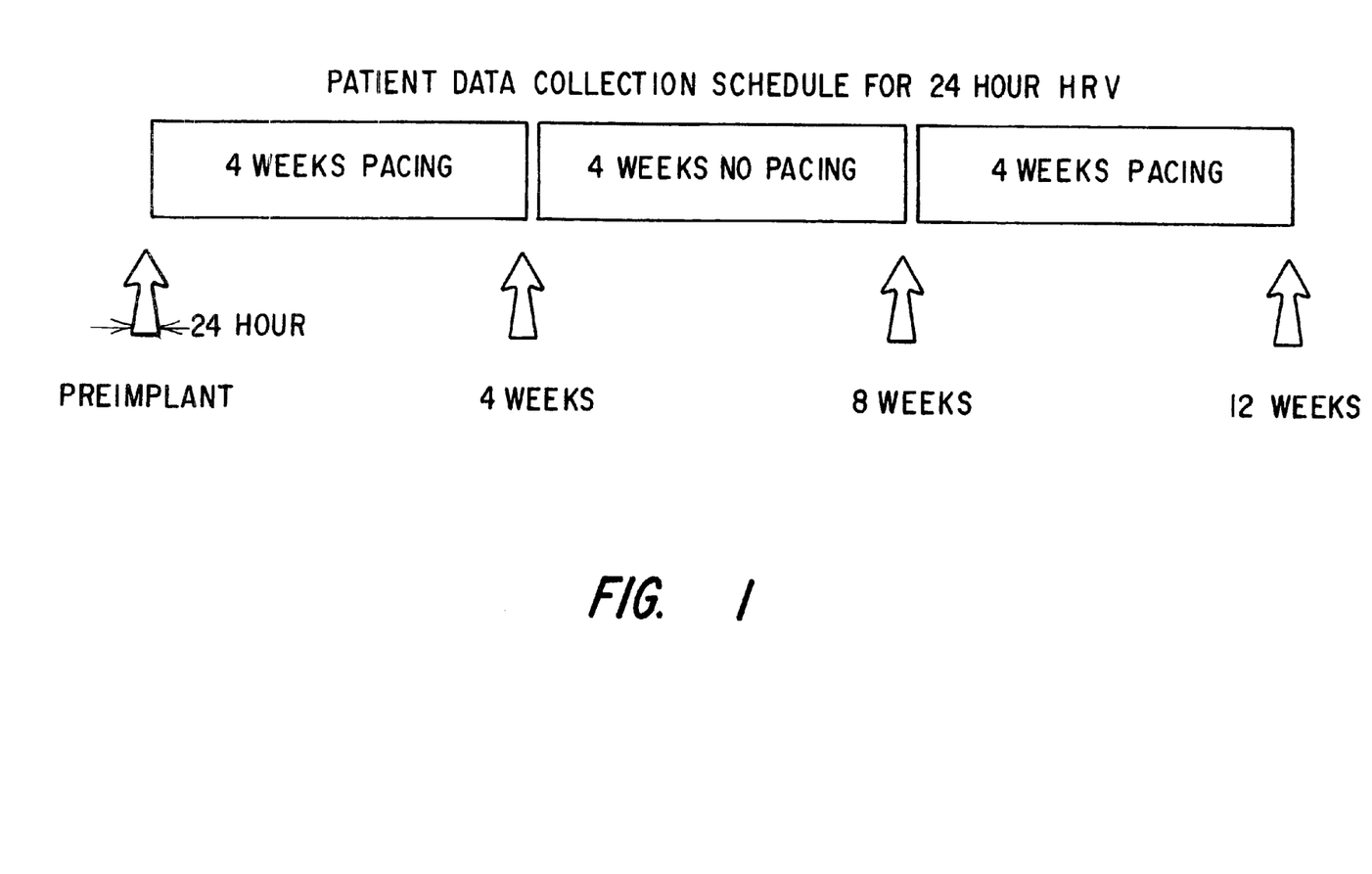
FIG. 1 is a graphical representation of a patient data collection schedule for ECG waveforms and $VO2_{max}$ measurements.

Referring to FIG. 1, there is graphically illustrated the data collection approach used in establishing the relationship between heart rate variability and $VO2_{max}$. Twenty-four hour surface ECG data was collected on seven CHF patients at four time points during a period of twelve weeks. Specifically, the data was collected just prior to the implant of a cardiac pacemaker, then again at the end of four weeks of pacing, at the end of four weeks of no pacing (eight weeks), and at the end of four weeks of pacing (twelve weeks). The pacing mode was randomized between best univentricular pacing and biventricular pacing, during the two four-week periods during which pacing took place. ECG data was sampled at 500 Hz and recorded on a modified 16-bit solid state digital holter recorder. At each of the four time points, the patients also performed symptom-limited maximal exercise tests. $VO2_{max}$, $VO2_{max}$ at the anaerobic threshold, maximum power attained and total exercise duration were some of the exercise parameters collected.

Figure 2:
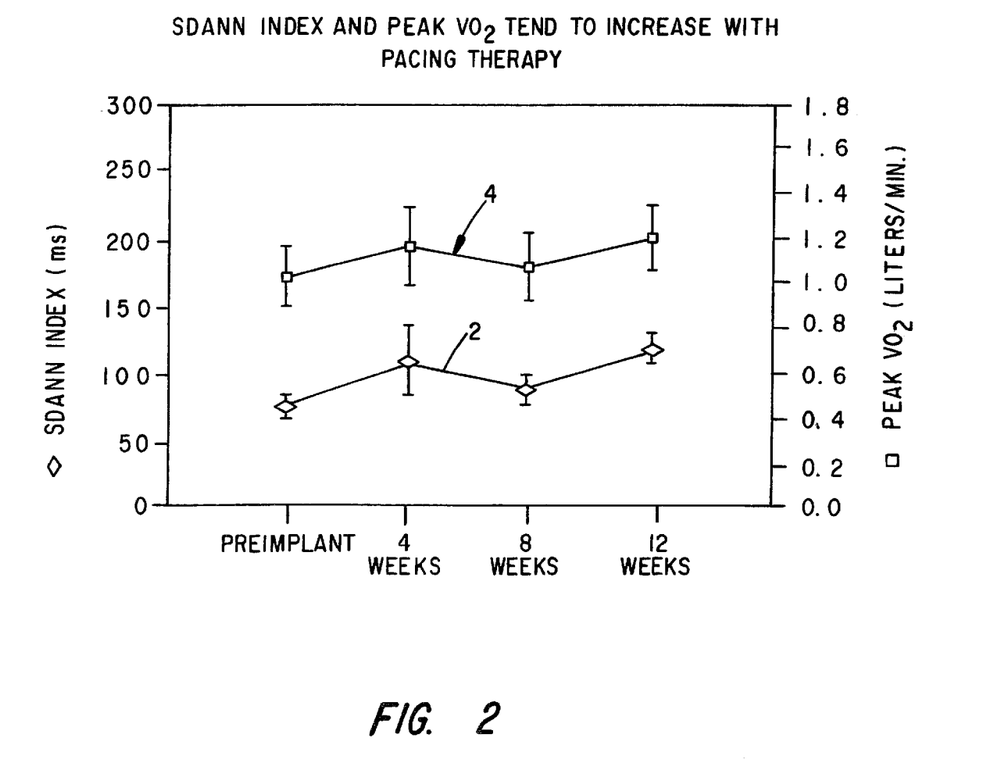
FIG. 2 is a plot of $VO2_{max}$ and the computed SDANN index plotted on the same time axis and showing the correlation of each as the pacing protocol is changed.

The surface ECG data was filtered to remove any premature ventricular contractions and other ectopic beats, to obtain normal RR intervals. Various HRV parameters were calculated from the measured and filtered RR intervals. The well-known SDANN index, which is the standard deviation of five-minute intervals averaged over 288 five-minute intervals in a 24-hour period, was computed for the four 24-hour sampling periods illustrated in FIG. 1. The SDANN indices for these four sampling periods are plotted as curve 2 in FIG. 2 and also plotted on the same graph as curve 4 are the values of $VO2_{max}$ measured at the same time. The change in SDANN index correlated well with the change in $VO2_{max}$. Also apparent is the fact that the pacing therapy proved effective in improving these patient's exercise capacity.

Figure 3:
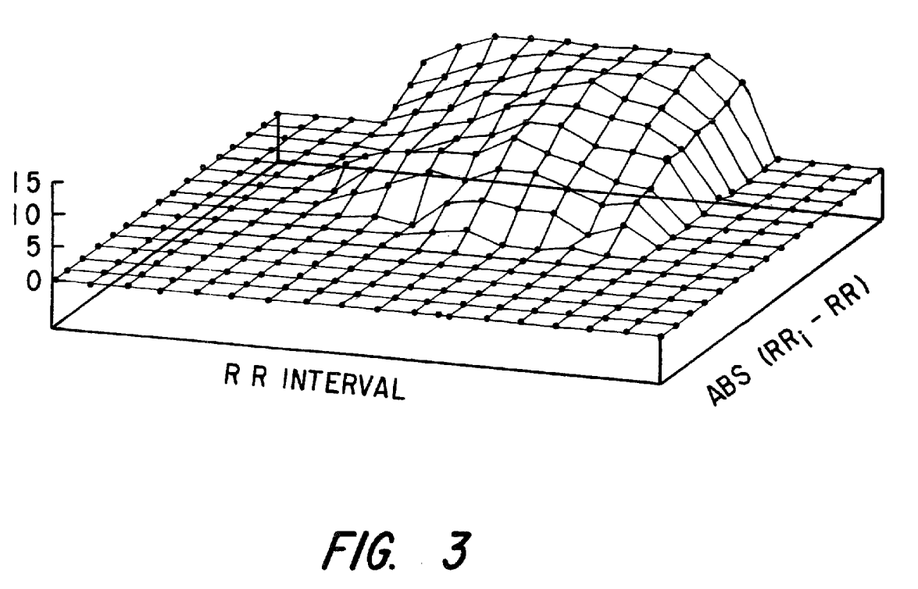
FIG. 3 is a pseudo three-dimensional histogram plot of RR interval vs. the absolute value of the difference in RR interval between successive heart beats.

The HRV data collected in accordance with the protocol of FIG. 1 was also plotted as a two-dimensional histogram where the RR intervals and absolute value of the difference between successive RR intervals are quantized into a plurality of bins and then plotted against one another as shown in FIG. 3. Through logarithmic compression, as described fully in U.S. Pat. No. 5,603,331, and which is hereby incorporated by reference, the frequency value to be plotted on the Z axis can be limited to a number of levels compatible with the amount of memory available.

Figure 4:
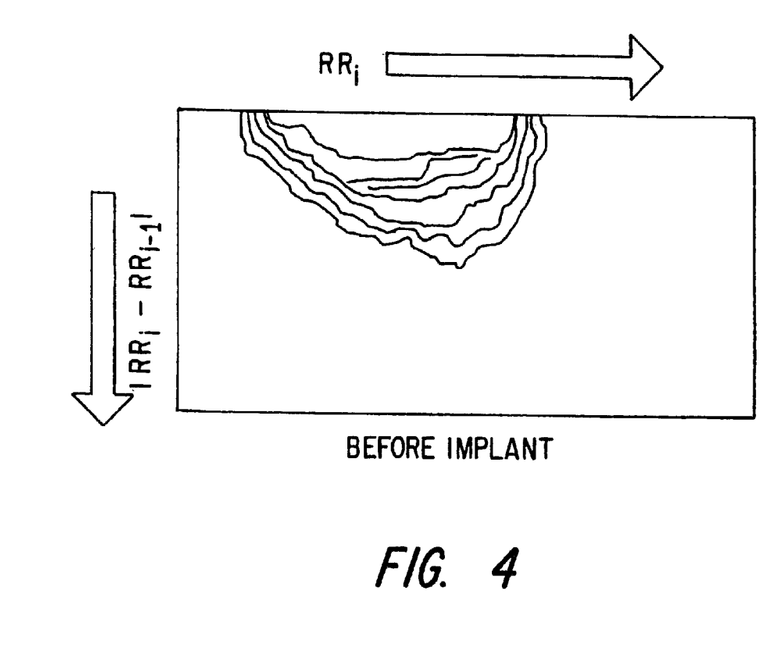
FIG. 4 is a two-dimensional histogram plot taken prior to pacer implant where frequency of occurrence of predetermined HRV values are represented by a gray scale.
Figure 5:
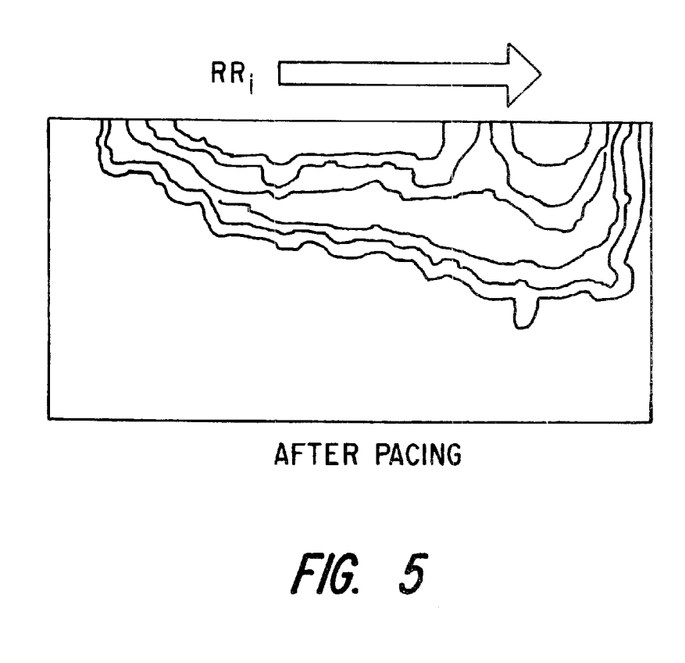
FIG. 5 is a plot like that of FIG. 4 but representing HRV data taken following four weeks of pacing therapy.
Figure 6:
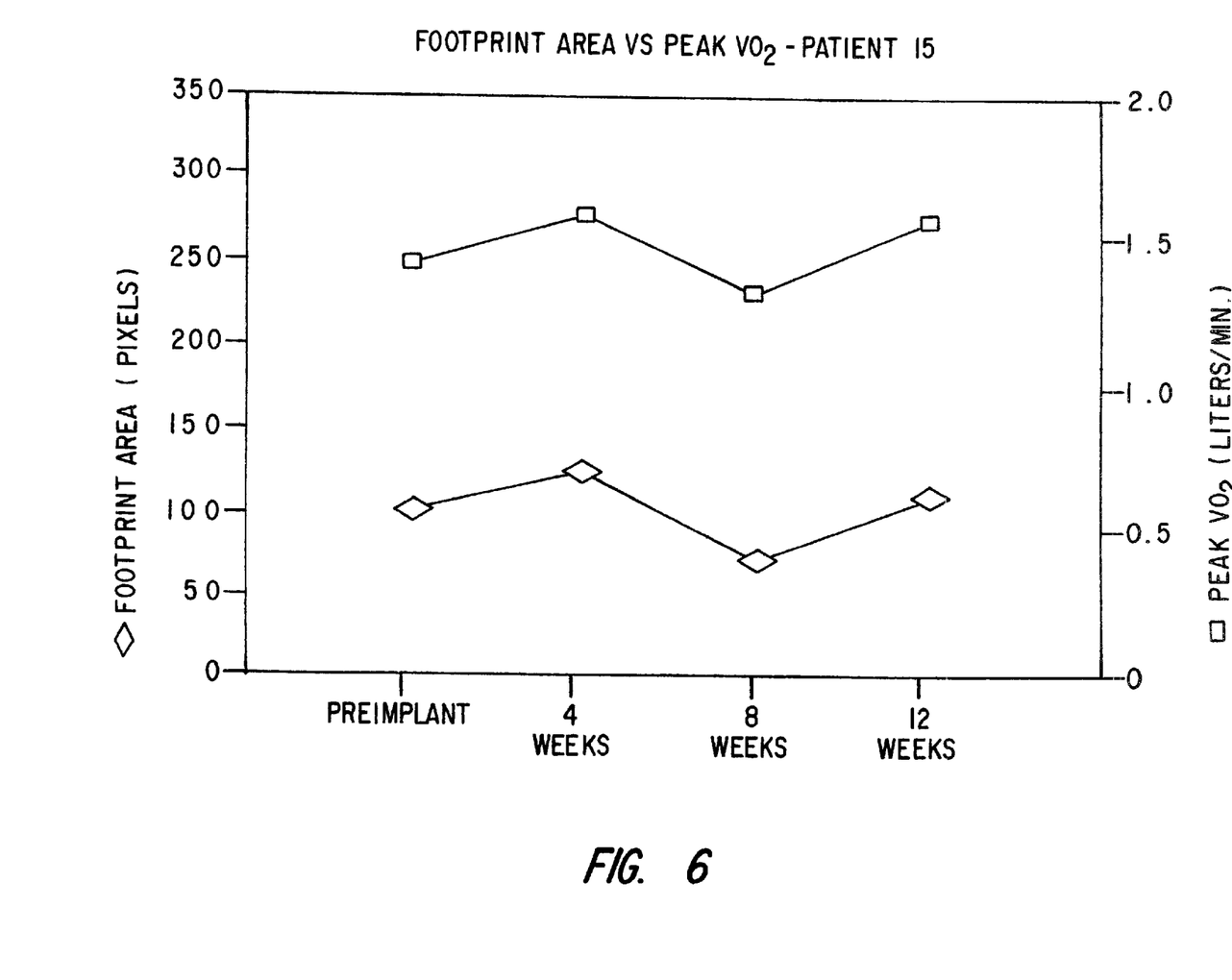
FIG. 6 is a plot showing the correlation between histogram of footprint size and $VO2_{max}$ for the data collection schedule of FIG. 1.

In the graphs of FIGS. 4 and 5, the histogram is plotted with a gray scale utilized to identify the frequency parameter. As in the case of FIG. 3, the RR interval number is plotted against the absolute value of the difference between successive RR intervals and rather than having the distance along a Z axis as a measure of the frequency value, a gray scale color is used instead. Thus, the plots of FIGS. 4 and 5 can be considered as contour maps of the pseudo three-dimensional histogram with different shades of gray representing various heights of the z axis found in the pseudo three-dimensional plot. We have found the area subtended by the plot, i.e., its footprint, to be an indicator of $VO2_{max}$ with changes in footprint area due to pacing also tracking changes in $VO2_{max}$. Comparing FIGS. 4 and 5, it is readily apparent that pacing the patient suffering CHF had the effect of increasing that patient's maximum exercise capacity. Footprint area is determined by counting the number of non-zero pixels in the two-dimensional plot.

Figure 7:
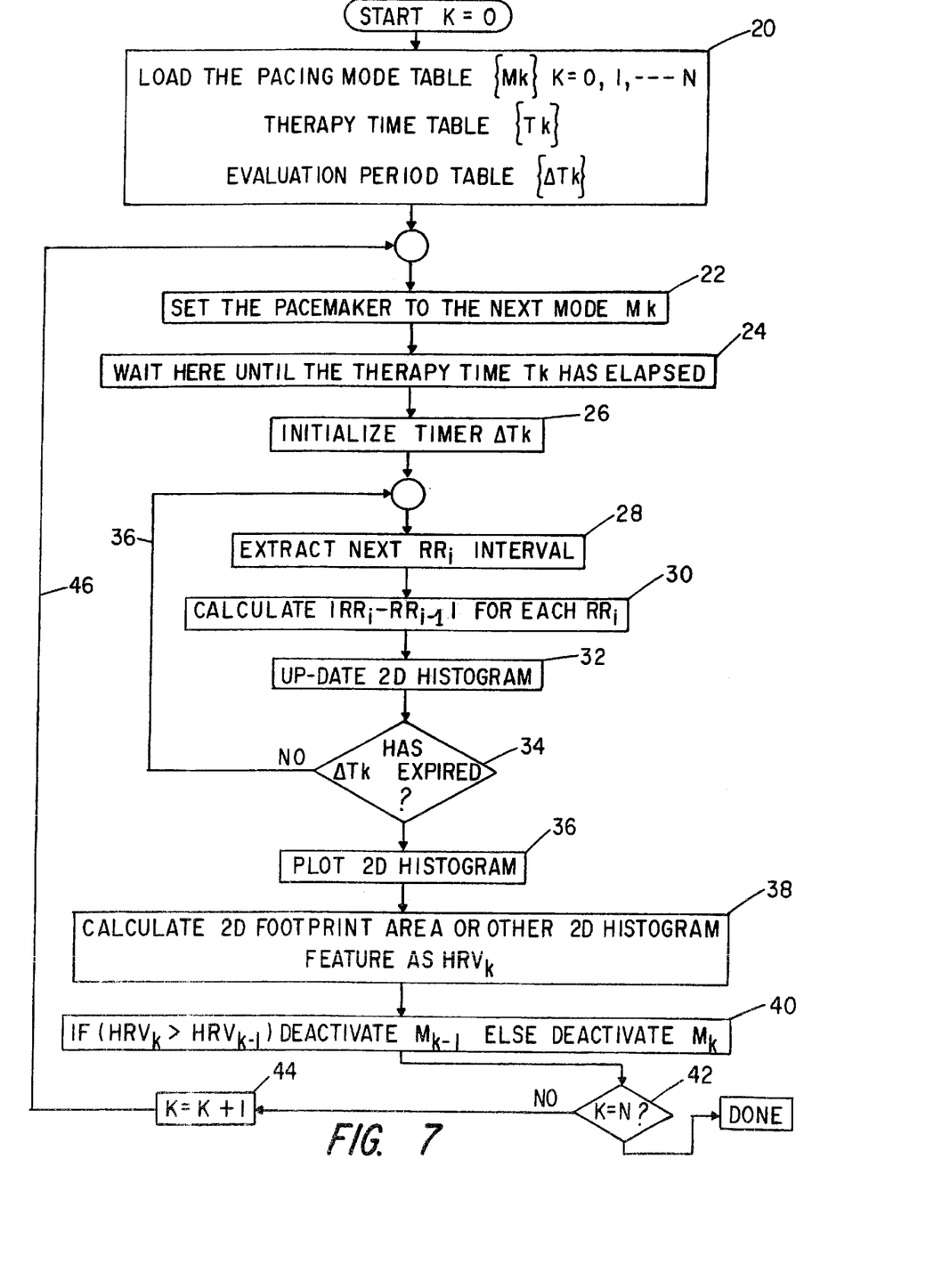
FIG. 7 is a flow chart of the algorithm for determining an optimum pacing mode based upon the relationship of HRV to peak oxygen uptake.

FIG. 7 is a software flow diagram for optimizing the pacing mode of an implantable programmable cardiac pacer based upon observed improvements in a patient's exercise capacity and which does not require cardiopulmonary exercise monitoring equipment in carrying out the method. This flow diagram is in sufficient detail such that a programmer of ordinary skill can write software code for allowing a microprocessor to carry out the indicated functions. Such microprocessor program may be implemented in the implantable pacemaker device itself or, alternatively, may comprise equipment external to the patient.

It is contemplated that the implantable pacemaker is of the type that allows its mode to be reprogrammed via a transcutaneous telemetry link. Most present-day pacemakers incorporate this capability. The first step in carrying out the process is to initialize a pacing mode table, a therapy time table and an evaluation period table as represented by block 20 in FIG. 7. The implanted pacemaker is capable of operating in a plurality of modes $M_k$, k=0, 1, . . . N. For example, a first mode may be VDD with a first AV interval and a second mode may be VDD with a second, different AV interval. A mode change may also be based upon the pacing site (or sites in the case of a biventricular pacemaker). In fact, any change in the pacing regimen may be assigned as a mode in the pacing mode table.

The therapy time $T_k$ determines the time that a mode change takes place and will typically be measured in terms of days, weeks or months. The evaluation period $\Delta T_k$ establishes the length of time over which heart rate variability data is collected and will typically be measured in terms of hours.

Once the initialization steps reflected in block 20 have been programmed, the pacemaker will be set to the first mode $M_0$ (block 22) and the patient will continue to be paced in accordance with that first mode until the therapy time $T_k$ has elapsed (block 24). At this time, the evaluation period timer $\Delta T_k$ is initialized to a starting point. With the evaluation period timer running, each RR interval ($RR_i$) is extracted from the ECG waveform (block 28) and repetitive calculations are made to measure heart rate variability as the absolute value of the difference between two successive RR intervals $|RR_i-RR_{i-1}|$. This is represented by block 30 in FIG. 7. Each time a new HRV value is computed, it is stored in an appropriate bin of a histogram memory (block 32). A test is then made at decision block 34 to determine whether the evaluation period $\Delta T_k$ has expired. If not, control loops back via path 36 to the input of block 28 so that steps 28, 30 and 32 are repeated iteratively until the time interval $\Delta T_k$ has expired.

At that point, the histogram is effectively plotted (block 36). Next, either the 2D histogram footprint area or some other feature of the 2D histogram is calculated as a measure of $HRV_k$, i.e., the heart rate variability measure for the particular mode involved. While the 2D histogram footprint area has been determined to be a measure of $VO2_{max}$, other features of the 2D histogram may also be indicative of $VO2_{max}$. For example, the slope of the diagonal that is tangent to the base of the 2D plot is believed to be an indicator of HRV as well.

Irrespective of the approach used in deriving $HRV_k$, as represented by block 40, the next step in the algorithm is to compare the current HRV measure with that earlier derived relating to the immediately previous mode to determine whether $HRV_k$ is greater than $HRV_{k-1}$. If it is, then the current mode is shown to have provided improved $VO2_{max}$ and the previous mode is discarded as an option. However, had the current heart rate variability index been less than the index derived for the previous mode, then the current mode would be disregarded.

As indicated by decision block 42, a test is made to determine whether all of the possible modes in the pacing mode table have been considered and, if not, the mode index is incremented (block 44) and control loops back over path 46 to the input of block 22 whereby the routine is repeated until all modes have been exercised.

We have determined, based upon patients' studies, that change in VO2$_{max}$ correlates directly with change in heart rate variability and that information concerning the patient's exercise capacity can be derived from ECG signals. Moreover, the patient's exercise capacity can be inferred from the SDANN index or, alternatively, from the area of the footprint of a two-dimensional histogram where heart rate variability is plotted against RR interval over a predetermined time interval.

Figure 8A:
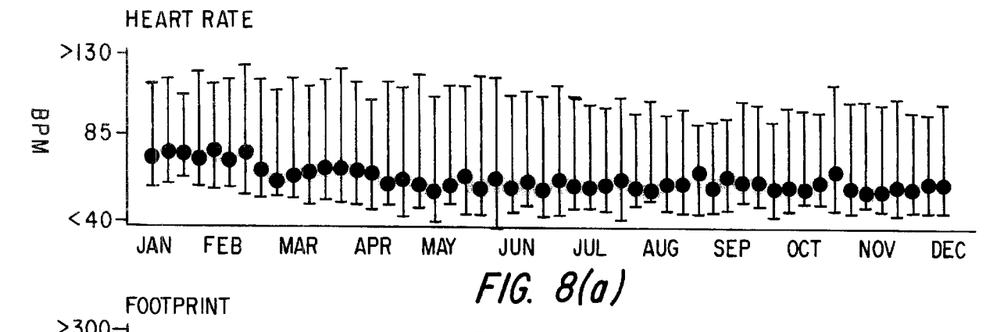
FIG. 8(a) is a plot of average heart rate, with maximum and minimum vales indicated, over a 52-week period.
Figure 8B:
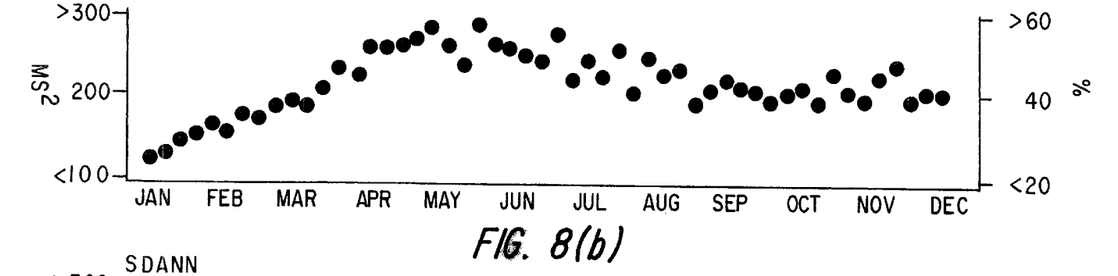
FIG. 8(b) is a plot of average weekly histogram footprint size (area) over the same 52-week period.
Figure 8C:
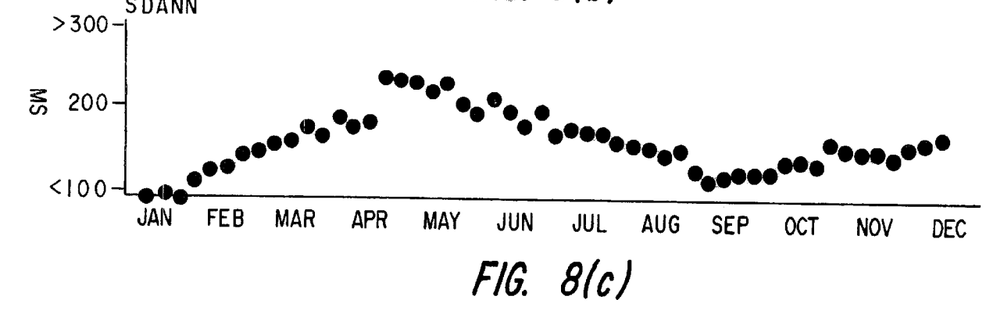

The present invention allows the plotting of HRV measures on a desired time scale and the resulting plot is deemed useful in assessing whether pacing therapy or drug therapy adjustments are beneficial. In FIG. 8(*a*), there is shown a plot of the average weekly heart rate of a patient over a 52-week period with the vertical lines passing through the average values indicating the range between the highest rate and the lowest rate for the week involved. Aligned with the plot of FIG. 8(*a*) are the plots of FIGS. 8 (*b*) and 8 (*c*). FIG. 8 (*b*) shows a corresponding plot of heart rate variability as measured by the footprint area method. FIG. 8(*c*) is a corresponding plot of heart rate variability for the same patient as measured by the SDANN index.

The rise in heart rate variability between January and April indicates that the therapy then being applied resulted in a beneficial increase in heart rate variability and, accordingly, an increase in peak VO$_2$ consumption. An apparent change in therapy in May had a negative result as reflected by a decrease in HRV. Thus, it is apparent from the trending data plotted in FIGS. 8(*b*) or 8(*c*) that the efficacy of a particular therapy can be evaluated with periodic adjustments being made so as to optimize peak VO$_2$ consumption and, therefore, the patient's exercise capacity.

In a practical system implementing the present invention, the plots of FIGS. 8(*a*) through 8(*c*) may be displayed on a computer monitor or, alternatively, may be printed out as hard copy from a printer.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, while the present invention has been described and illustrated in connection with patient therapy being carried out by electrical stimulation from an implantable pacemaker, it is also contemplated that the different therapy modes can be based on the administration of various drugs where such drugs have an influence on cardiac performance. Thus, the mode table can include a series of different drugs or the same drug but with differing dosages. Periodically, and in accordance with the entries in the therapy time table and the evaluation period table, the drug therapy mode would be changed and the effect on HRV, as measured by SDANN or a feature of the 2D histogram used to assess the efficacy of each mode.

What is claimed is:

1. A method of optimizing a mode of therapy applied to a patient, comprising the steps of:

(a) measuring and recording ECG waveforms over a predetermined time interval at a first point in time;

(b) computing from said ECG waveforms the absolute value of the difference in the length of successive RR intervals;

(c) plotting a two-dimensional histogram of the values computed in step (b) vs. RR intervals;

(d) measuring the area subtended by the plot of step (c) as an indicator of a patient's exercise capacity;

(e) subsequently changing the mode of therapy applied to the patient;

(f) repeating steps (a) through (d) at a later time;

(g) plotting a value of the area measured in step (d) at the first point in time and at the later time to display trends in the patient's exercise capacity.

(h) comparing the area measured in step (d) at the first point in time to the area measured in step (d) at the later time to assess which area is the greater; and (i) adjusting the mode of therapy to increase the patient's exercise capacity.

* * * * *